United States Patent [19]

Rabenau et al.

[11] Patent Number: 5,318,583
[45] Date of Patent: Jun. 7, 1994

[54] LANCET ACTUATOR MECHANISM

[75] Inventors: Richard Rabenau, Arab; Rowland W. Kanner, Guntersville, both of Ala.

[73] Assignees: Ryder International Corporation, Arab, Ala.; Boehringer Mannheim Corp., Indianapolis, Ind.; a part interest to each

[21] Appl. No.: 878,736

[22] Filed: May 5, 1992

[51] Int. Cl.$^5$ .............................................. A61B 17/32
[52] U.S. Cl. ................................................... 606/182
[58] Field of Search ............................. 606/181–183; 128/770; 604/136–139, 157

[56] References Cited

U.S. PATENT DOCUMENTS

| | | |
|---|---|---|
| 2,061 | 4/1841 | Van Osdel. |
| 4,924,879 | 5/1990 | O'Brien ........................... 128/770 |
| 5,035,704 | 7/1991 | Lambert et al. ................... 606/182 |

Primary Examiner—Jerome E. Kruter
Attorney, Agent, or Firm—Trexler, Bushnell, Giangiorgi & Blackstone, Ltd.

[57] ABSTRACT

An actuating mechanism for sequentially advancing and retracting a lancet needle includes a carriage for carrying the advancement and retraction of the needle, and a cam-following structure for transmitting propulsion to the carriage during the advancement. The actuating mechanism is also provided with a drive cam structure which engages the cam-following structure to direct the advancement propulsion. The cam-following structure can have a separate surface engagable with the drive cam structure during the retraction of the carriage and during arming of the actuator for the advancement propulsion.

23 Claims, 6 Drawing Sheets

LANCET ACTUATOR MECHANISM

BACKGROUND OF THE INVENTION

This invention relates to lancet devices for use by physicians and technicians or the patient to extract a blood sample, and more particularly relates to a mechanism for effecting the initial puncture and thereafter retracting the lancet needle following the skin puncturing procedure, all of which is done with smooth, linear movements to minimize patient discomfort and pain.

In order to reduce trauma to the patient during blood sampling procedures, automated finger lancet devices have been developed which eliminate the patient's view of both skin puncture and the lancet needle or blade itself as described for example in U.S. Pat. Nos. 4,553,541 and 4,577,630. In U.S. Pat. No. 4,892,097, the lancet needle can be housed within a small device which provides a spring-driven mechanism for thrusting and retracting the needle. While such devices obstruct the patient's view, considerable patient discomfort has been experienced when all lateral motion of the lancet needle is not prevented. This disadvantage is eliminated by the lancet actuator in accordance with the present invention which provides improved patient comfort in that initial puncture and withdrawal of the lancet needle is effected in a continuous, smooth rapid motion so that little or no lateral movement can take place. The present invention is an improvement on the lancet actuator described in U.S. Pat. No. 5,196,025 the disclosure of which is incorporated by reference herein.

SUMMARY OF THE INVENTION

In accordance with the present invention, an actuating mechanism for sequentially advancing and retracting a lancet needle includes a carriage for the advancement and retraction of the lancet, and a cam-following structure for transmitting propulsion forces to the carriage during the advancement. The actuating mechanism is also provided with a drive cam structure which engages the cam-following structure to produce and direct the advancement propulsion. The cam-following structure has a separate cam surface engagable with the drive cam structure during the retraction of the carriage.

In a preferred embodiment, the carriage and the cam-following structure are integrally molded, and the drive cam structure pivots against a first cam surface of the cam-following structure during generation of the propulsion forces, sequentially followed by continued pivotal movement against a second surface of the cam-following structure during retraction. The actuator is armed or cocked in a reversing pivotal movement of the drive cam structure during which the drive cam structure engages the two surfaces of the cam-following structure in reverse sequence relative to the advancement and retraction during the actuator operation of the lancing procedure.

DESCRIPTION OF THE ILLUSTRATED EMBODIMENT

Figure 4:
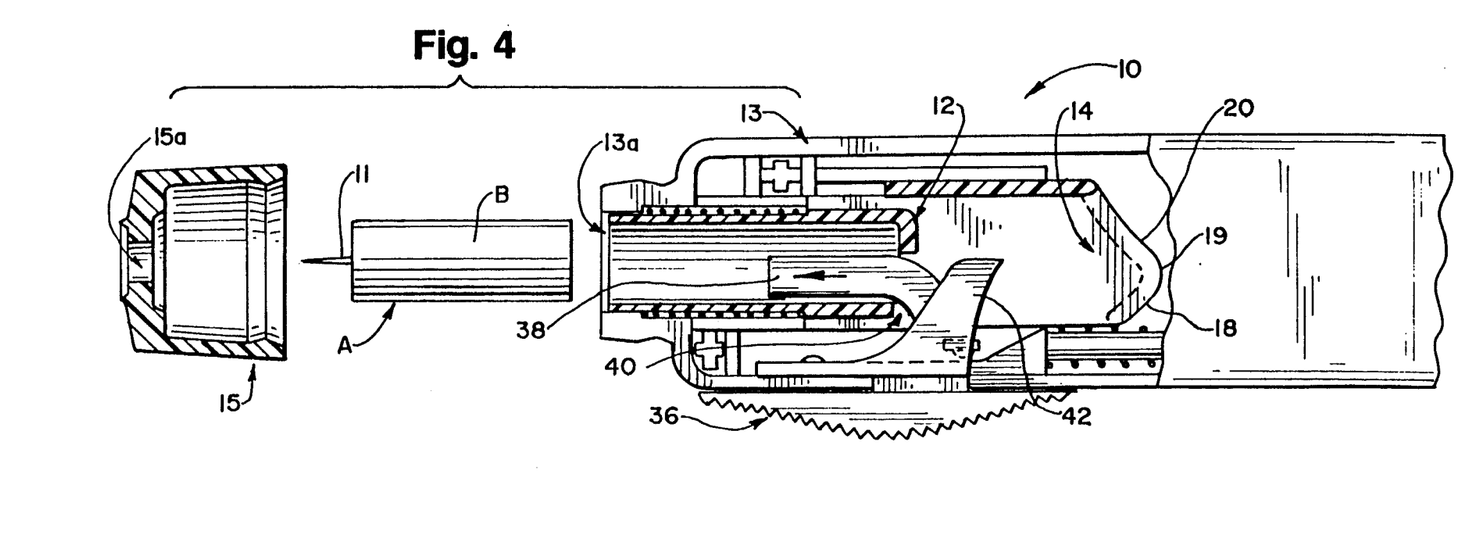
FIG. 4 is a fragmentary sectional view similar to FIGS. 1-3 and illustrating removal of a lancet unit from the device.
Figures 5, 6, 7:
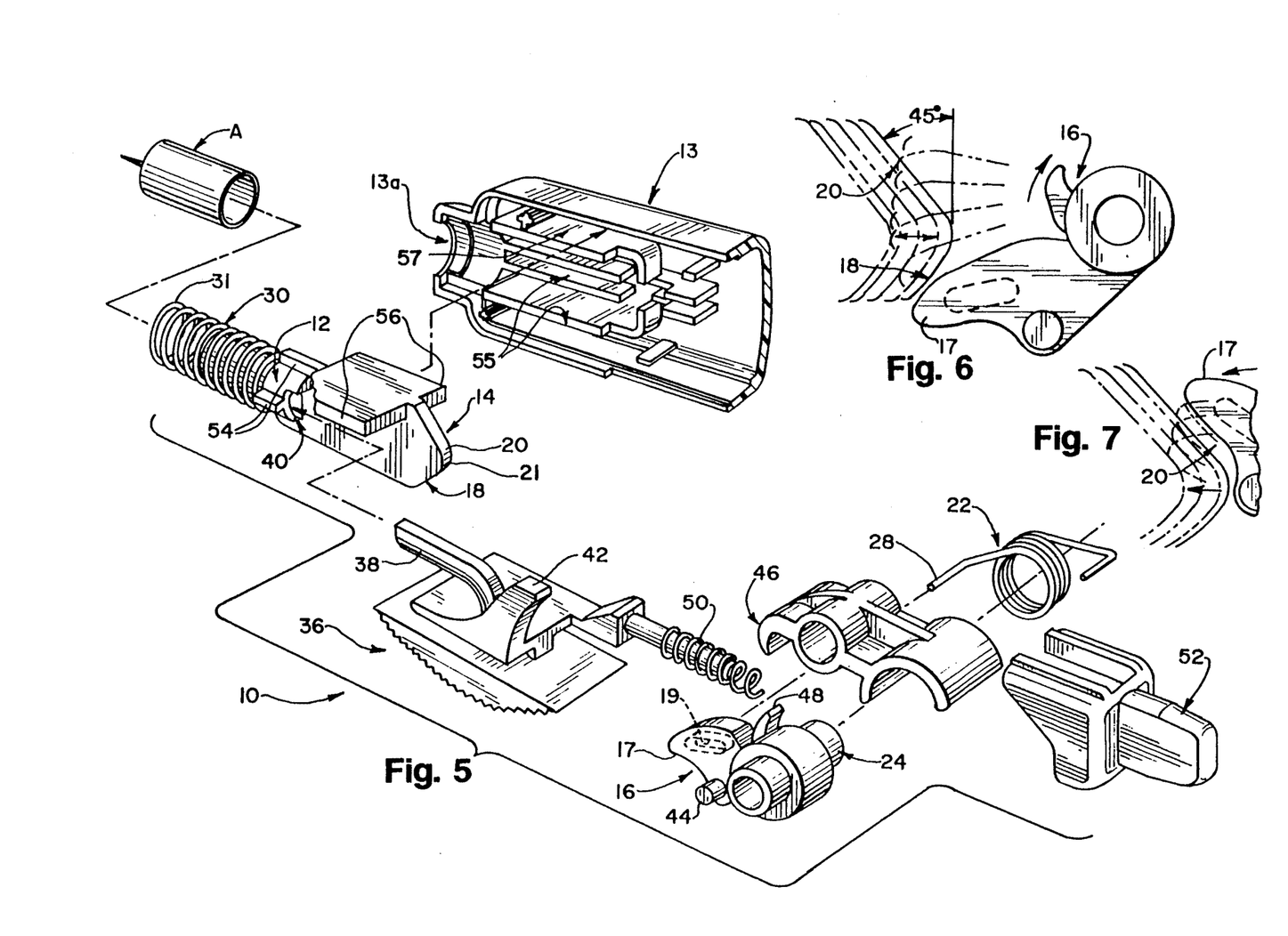
FIG. 5 is an exploded perspective view of the actuator mechanism of the device in FIGS. 1-4.
FIGS. 6 and 7 are enlarged, fragmentary views of the reversible sequences of pivoting cam structure within the actuator mechanism shown in FIGS. 1-5.
Figure 8:
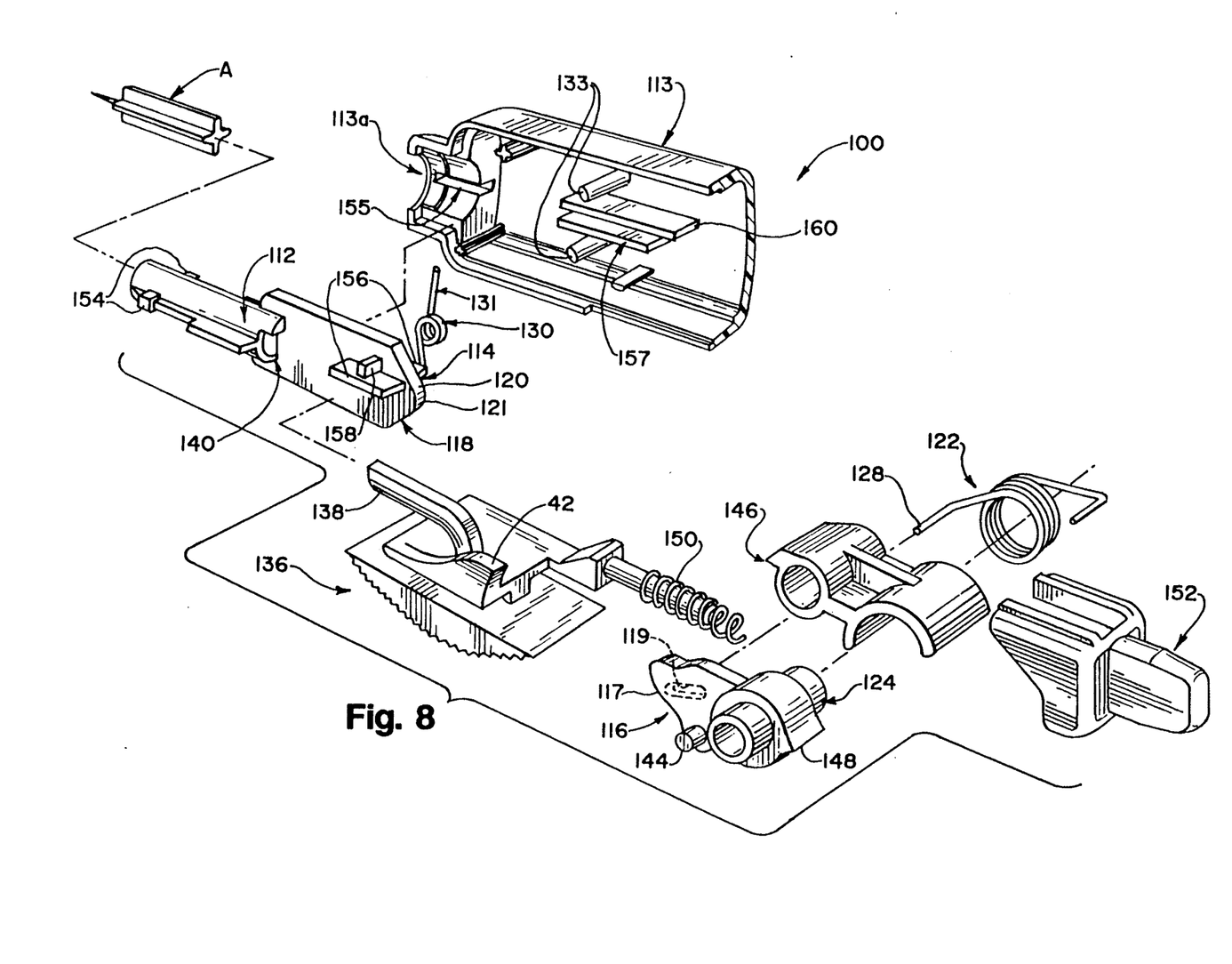
FIG. 8 is an exploded perspective view of a second embodiment of an actuator mechanism in accordance with the present invention.

Referring initially to FIGS. 4 and 6, an embodiment of a lancet actuator in accordance with the present invention is generally designated by reference character 10. The actuator 10 accommodates the use of conventional, disposable lancet needle-and-support-body units A. The units A comprise a metal needle 11 carried by a molded plastic body B. A lancet unit A is inserted into a lancet holder or carriage means 12 within the actuator 10, as more fully described hereinafter, prior to operation of the actuator 10 to puncture a patient's tissue in a blood sample extraction procedure, after which the lancet unit A is removed from the holder or carriage 12 for disposal. In the actuator 10 of the illustrated embodiment, a split housing 13 (one half only shown) has an access and operation aperture 13a formed at one end, through which the disposable lancet unit A is inserted and removed. The actuator 10 also has a cap 15 which is snap-fitted to the housing 13 to cover the aperture 13a and the inserted lancet unit A during the blood extraction procedure, and therefore the cap 15 will be exposed to the blood sample and will consequently be disposable with the used lancet unit A. The cap 15 includes an opening 15a through which the needle 11 of lancet A can project. The extension of the cap 15 determines the length of the projection of the needle portion 11 therefrom, and therefore also determines the puncture depth when the cap 15 is seated on the donor's skin.

FIG. 4 illustrates the mechanism of the actuator 10 preparatory to insertion of the lancet unit A and before the actuating mechanism has been cocked to prepare the actuator for operation. As can be appreciated, this condition of the actuator 10 also corresponds to that as would occur after completion of a prior procedure. Thus, the lancet unit A is positioned within the carriage or holder 12 and the cap 15 is snapped into place. The actuator is then cocked to arrive at the position shown in FIG. 1, as explained more fully hereinafter, and is thus ready for operation.

Figure 1:
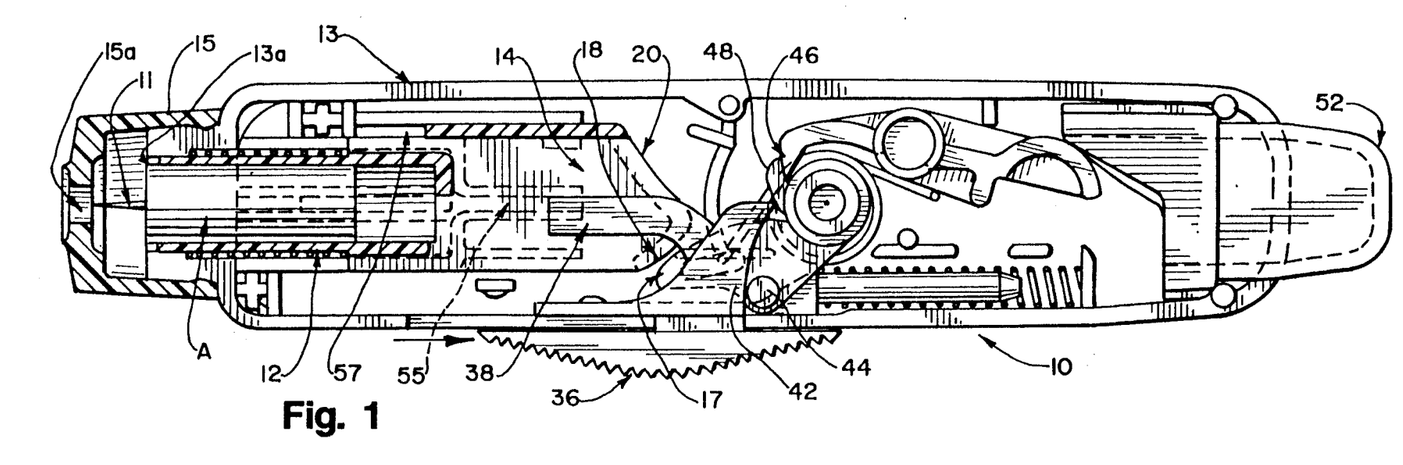
FIG. 1 is a cross sectional view of the first embodiment of a lancet actuator device in accordance with the present invention.
Figure 2:
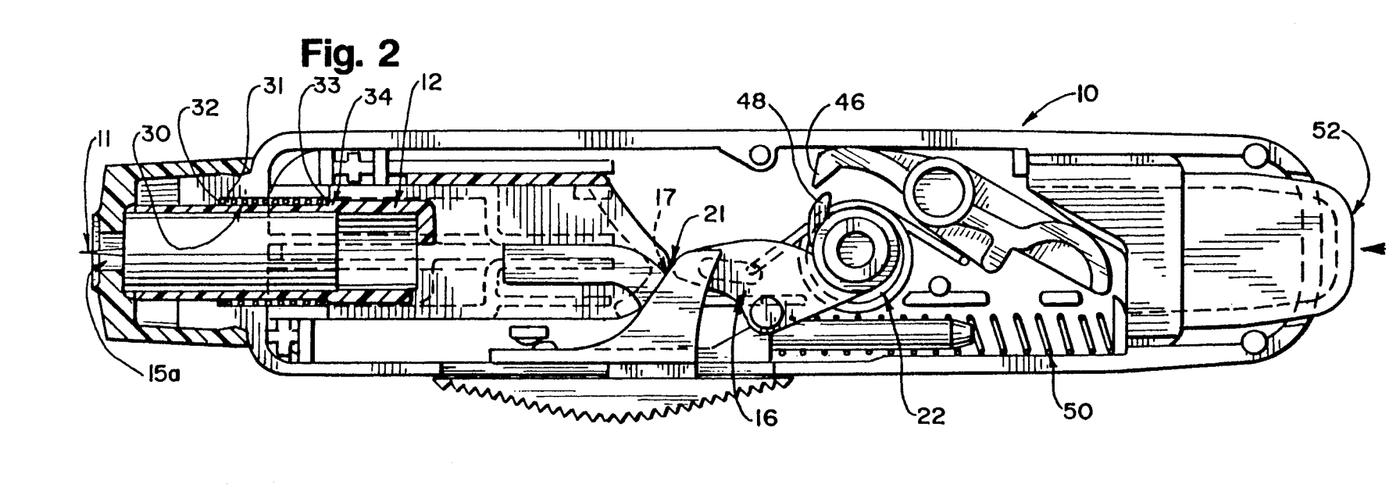
FIGS. 2 and 3 are sectional views similar to FIG. 1 illustrating sequential operating positions of the actuator mechanism of the device.
Figure 3:
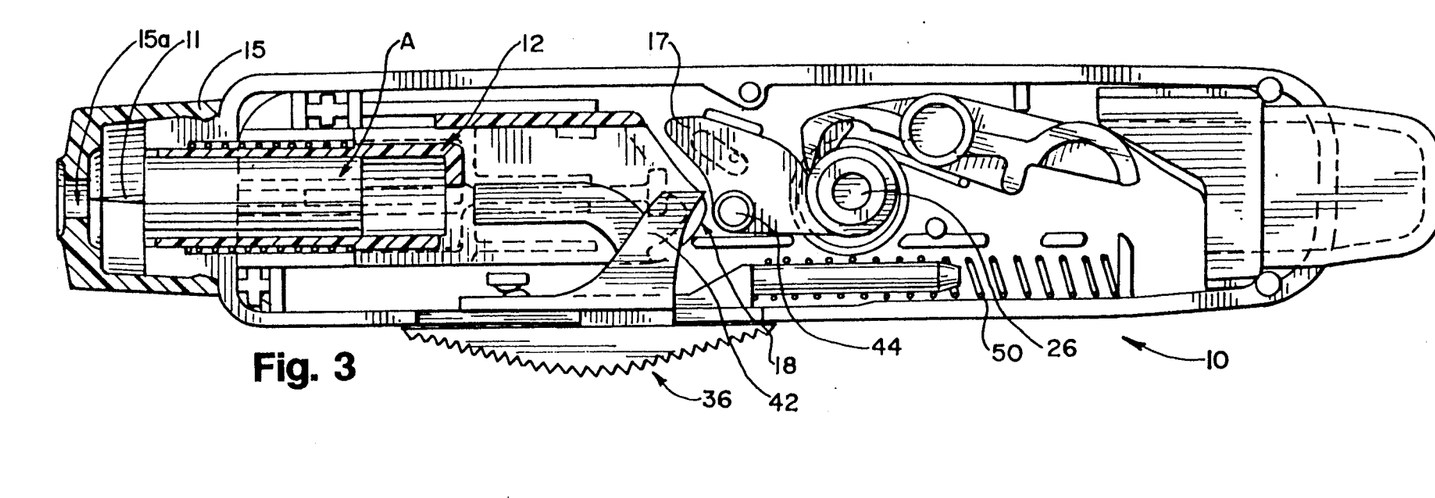

In operation of the actuator 10, the lancet holder 12 carries the lancet unit A from the retracted position shown in FIG. 1 to the linearly advanced position shown in FIG. 2 in which the lancet needle 11 projects from the opening 16 to puncture the tissue, and then immediately retracts the lancet unit A into the position shown in FIG. 3. FIGS. 1, 3 and 4 illustrate the same retracted position of the holder 12, although FIG. 4 also shows the cap 15 detached and lancet unit A removed from the holder 12. The advancement and retraction of the lancet needle is not only linear, but is attained with a rapid, smooth movement to minimize patient discomfort.

In the illustrated embodiment, the lancet holder-carriage 12 is integrally molded and connected with a cam-following structure 14 which transmits propulsion to the holder 12 for the advancement of the lancet unit A and needle 11. A pivoting, drive cam structure 16 has a cam arm 17 which is engagable with the cam-following structure 14 in a wiping, cam action to propel the linear advancement of the cam-following structure 14 and holder 12 for the needle puncturing motion. The cam-following structure 14 has a propulsion cam surface 18 which is translated by the propelling clockwise pivot of the drive cam structure 16 and arm 17 (FIG. 6) between the position in FIG. 1 and the position in FIG. 2. The cam-following structure 14 also has a cocking cam surface 20 against which the cam arm 17 is engaged as the cam arm 17 continues in clockwise rotation from the position of FIG. 2 to the position of FIG. 3 when the cam-following structure 14 and holder 12 are retracted in reverse motion along the highly linear path and the lancet needle 11 is withdrawn from the tissue puncture. In the terminal position of holder advancement and needle penetration of FIG. 2, arm 17 is engaged with an arcuate, apex surface 21 which medially joins the propulsion and cocking cam surfaces 18 and 20.

The clockwise rotation of the drive cam structure 16 and arm 17 is driven by a torsion spring generally designated by reference character 22 which is wound around a hub portion 24 of the drive cam structure 16. The hub portion 24 is journaled on a stationary pivot bearing pin 26 which projects inwardly from the housing half 14 as shown in FIGS. 1-4. The cam arm 17 has a slot 19 which receives the movable end 28 of the torsion spring 22 so that the end 28 bears against and drives the clockwise rotation of the arm 17 (and the needle advancement stroke) as the torsion spring 22 unwinds. In addition, the advancement stroke of the cam-following structure 14 and holder 12 also compresses a coil spring 30 which surrounds the forward portion of the holder 12; as best shown by comparison of FIGS. 1 and 2, the stationary end 31 of the spring 30 is seated on an annular shoulder 32 formed by the housing halves 14, and the movable spring end 33 is secured to an annular shoulder 34 formed on the exterior and midway along the holder 12. The compression of the spring 30 produced by the advancement of the holder 12 is then releasable with expansion to provide the propulsion of the retraction stroke of the holder 12 as the drive cam arm 17 slides past the arcuate, apex surface 21 (which medially joins surfaces 18 and 20) and begins to slide against the cocking cam surface 20 as the cam arm 17 continues the clockwise pivot driven by the torsion spring 22. As a result, the expansion of the return spring 30 provides a smoothly continuous retraction of the holder 12 immediately following its advancement so that the puncturing thrust of the lancet needle 11 is rapidly reversed on the same highly linear path which suppresses patient discomfort.

When the lancet puncture procedure is completed with full retraction of the holder 12 into the position shown in FIG. 3, the used lancet unit A is ejected from the holder 12 by manually sliding the cocking structure 36 forwardly to the left from its neutral position as shown in FIG. 3 into the forward position shown in FIG. 4 so that the ejector arm 38 enters and passes through the slot 40 formed through the rear end of the holder 12. The ejector arm 38 thereby engages and displaces the lancet body B for removal through the entrance of the holder 12. The cocking structure 36 is then manually retracted to the neutral position shown in FIG. 3 so that the ejector arm 38 is withdrawn from the slot 40, after which a new lancet unit A can be inserted into the holder 12. The ejector arm 38 is arranged in laterally offset longitudinal alignment in relation to the cam surfaces 18 and 19 to enable relative clearance therebetween.

After installing the new lancet unit A, and preparatory to the next blood sampling procedure, the actuator 10 remains in the position shown in FIG. 3 and must be armed in a cocking operation to achieve the position shown in FIG. 1 in readiness for a succeeding lancing procedure. In this regard, the lancet can be installed either before or after the unit is cocked. In the arming or cocking operation, the cocking structure 36 is slidably displaced rearwardly to the right from the position shown in FIG. 3 so that the cocking arm 42 thereof is moved into engagement with a transversely projecting cocking pin 44 extending from the drive cam structure 16 below the cam arm 17. Continued manual motion of the cocking structure 36 causes the engagement with the cocking pin 44 to pivot the drive cam structure 16 counterclockwise so that the cam arm 17 moves downwardly from the position shown in FIG. 3 to the position shown in FIG. 1. As a result, the torsion spring end 28 is pivoted with the cam arm 17 winding and energizing of the torsion spring 22; when the counterclockwise, cocking pivot of the drive cam structure 16 reaches the position shown in FIG. 1, the end of the pivotal latch structure 46 drops into engagement behind a latch foot 48 radially projecting from the drive cam structure 16 and the tension in the wound torsion spring 22 maintains the latching engagement of the foot 48 against the latch 46. Thereafter, the return spring 50 which was compressed by the rearward motion of the cocking structure 36 expands to return the manually released cocking structure 36 once again to the neutral position shown in FIG. 3.

During the arming or cocking operation shown in FIG. 7, the counterclockwise pivoting cam arm 17 engages the cocking surface 20 so that the entire cam-following structure 14 and holder 12 are driven in linear advancement similar to the primary lancing advancement thereof. However, the cocking surface 20 forms a larger angle of approximately 45° relative to vertical in comparison with the corresponding angle of approximately 30° formed by the propulsion surface 18, in order to minimize the initial cocking strain manually required to wind the torsion spring 22 and promote uniformity of the manual cocking load which adds compression of coil return spring 30 to the winding of torsion spring 22. In addition, the contour of particularly cam surface 18 can be variably fabricated to enable uniform speed of the holder 12 advance and needle thrust.

When the arming or cocking operation has been completed as shown in FIG. 1, the cam arm 17 is slightly spaced from the propulsion cam surface 18 to ensure that the integral cam-following structure 14 and holder 12, and the needle 11, are fully retracted under the bias of the expanded spring 30. In order to actuate the lancing procedure and release the propulsion of the holder advancement, the trigger structure 52 is manually depressed inwardly as shown in FIG. 2 causing pivot of the latch end 46 so that it disengages from the cam foot 48 on the drive cam structure 16 which then pivots counterclockwise into engagement with the propulsion cam surface 18 as described hereinabove, under the force of the unwinding torsion spring 22. When the surface of the cap 15 has been placed against the donor's skin, the cam-driven advancement of the holder 12 thrusts the lancet needle 11 through the cap opening 16 to puncture the skin in the actuator position of FIG. 2 showing the maximum advancement corresponding to the maximum skin puncture depth. In order to ensure the accurately linear longitudinal path during the advancement and smooth retraction of the holder 12 and lancet unit A, the holder 12 and integral cam-following structure 14 are provided with laterally projecting and longitudinally extending guide flanges 54 and 56 which are slidably displaceable through corresponding slots 55 and 57 (or guide flanges) formed in the housing halves (13). The guide flanges 54 and 56 and slots 55 and 57 also stabilize the linear path of the holder 12 against any slight transverse torque components which could be generated by the wiping pivot of the cam arm 17 against the cam surfaces 18 and 20 of the cam-following structure 14. Consequently, the stabilized and guided holder 12 does not experience any lateral motion so that the lancet needle 11 enters and withdraws from the skin in smoothly continuous motions suppressing penetration trauma and donor discomfort.

Referring now to FIGS. 8-12, a second embodiment of the actuator in accordance with the present invention is generally designated by reference character 100; additional reference characters of the second actuator embodiment generally correspond to similar reference characters and features of the first embodiment 10.

Figure 9:
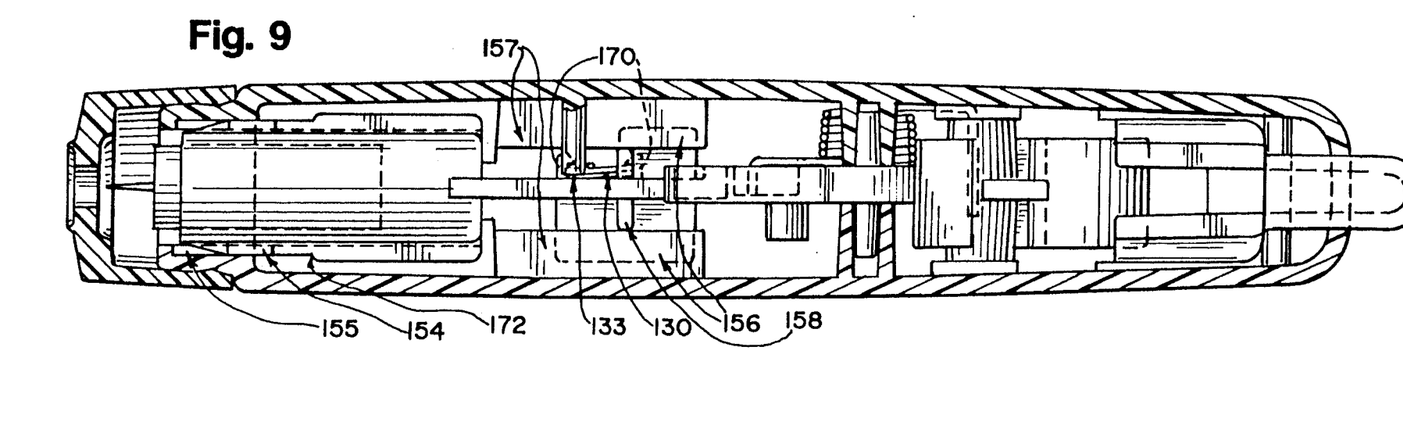
FIG. 9 is a partial sectional view from above illustrating the assembled actuator mechanism of FIG. 8.
Figure 10:
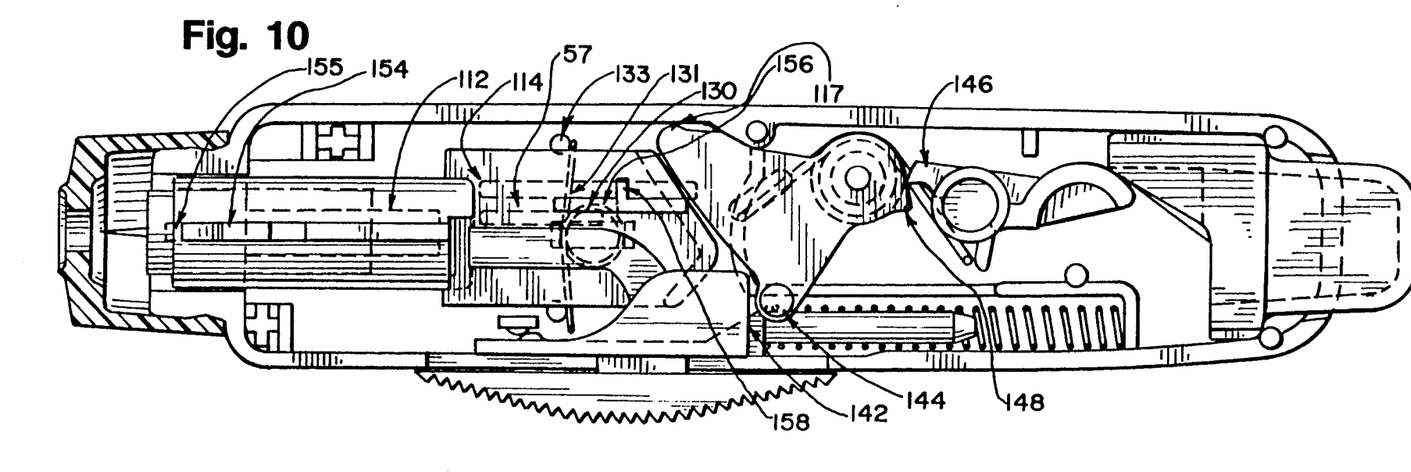
FIG. 10 is a vertical sectional view of the actuator mechanism shown in FIGS. 8 and 9.
Figure 11:
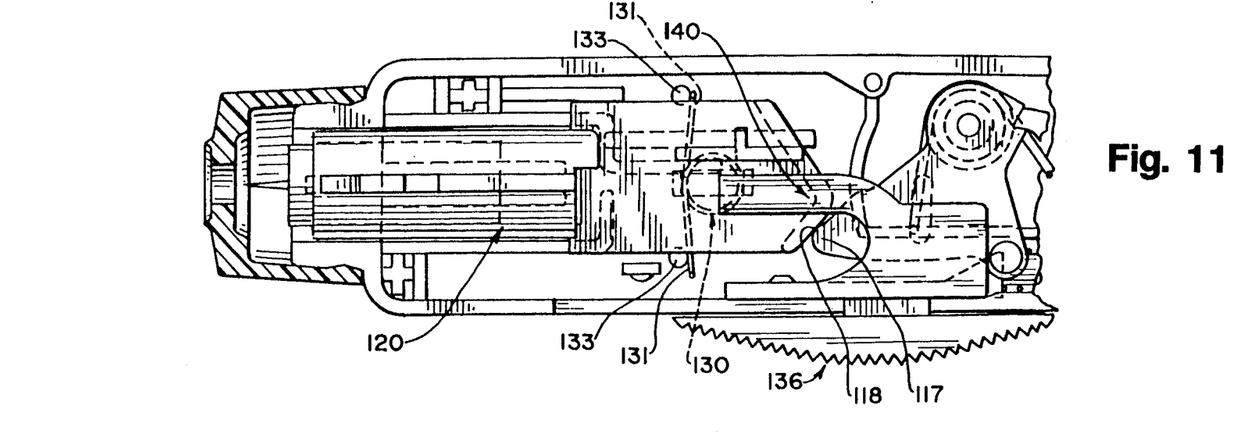
FIGS. 11 and 12 are fragmentary views similar to FIG. 10 illustrating sequential operating positions of the actuator mechanism shown in FIGS. 8-10.
Figure 12:
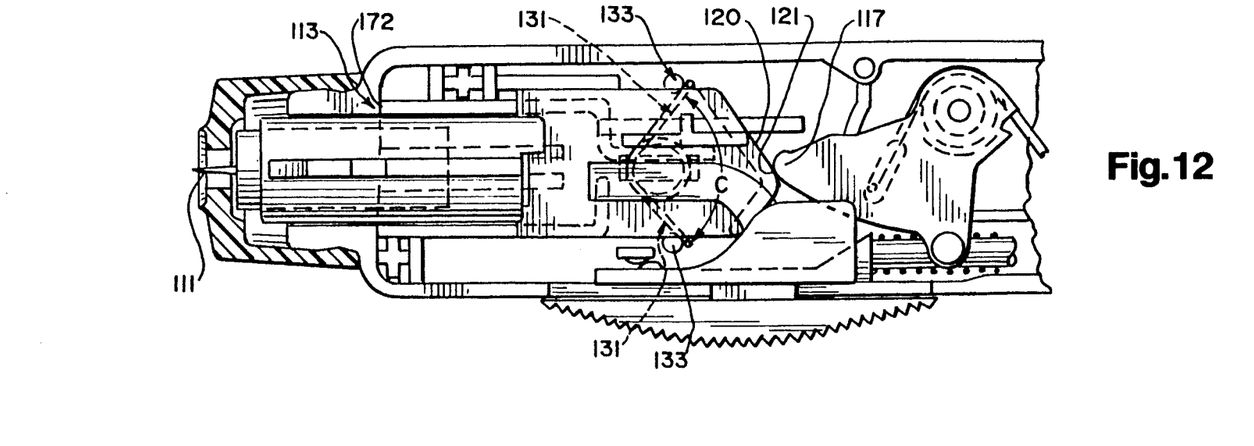

In the actuator 100, the return spring 130 is a torsion spring which is wound and carried on the cam-following structure 114. The wound portion of the torsion spring 130 is inserted between retainer arms 170 laterally projecting from the side of the cam-following structure 114. The two linearly projecting ends 131 of the torsion spring 130 respectively bear against upper and lower bearing pins 132 internally projecting from the housing half 113 as best shown in FIGS. 9 and 10. In operation of the torsion return spring 130, as best shown in FIGS. 11 and 12, the linearly projecting ends 131 of the spring 130 extend in generally vertical configuration as the cam arm 117 begins engagement against the propulsion surface 118 of the cam-following structure 140 as the advancement of the holder 120 is initiated as shown in FIG. 11. As the advancement of the cam-following structure 140 and holder 120 progresses, the wound portion of the torsion spring 130 is correspondingly carried forward on the cam-following structure 140; however, the stationary bearing pins 133 on the housing 113 cause the linear spring ends 131 to pivot and flex in angular configuration C in FIG. 12 as the cam arm 17 reaches engagement against the medial cam surface 121 at the terminal position of holder advancement and needle penetration 111. Thereafter, the further pivot of the cam arm 117 in withdrawal from the cocking cam surface 120 allows release of the flexure in the spring ends 131 to drive the retraction of the holder 120 as the ends 131 return to the generally vertical configuration at the completion of the withdrawal stroke. The reverse pivoting of the cam arm 117 during the cocking operation, corresponding to the description of the first actuator embodiment 10, also produces flexure of the spring ends 131 in similar manner. A shoulder 172 formed on the holder 120 provides a positive stop against the housing 113 to limit forward travel of the holder 112.

With the compact mounting of the spring 130 on the cam-following structure 114, the holder 112 can be provided with guide flanges 154 which laterally project adjacent to the forward end of the holder 112 and the guide flanges 54 are slidably displaceable through corresponding slots 155 forwardly located in the housing halves (113) adjacent to the operation aperture 113a. The guide flanges 154 provide additional axially symmetrical balance as well as extending the accuracy of the linear guidance particularly as the holder 112 is in transition from advancement to retraction. The lateral guide flanges 156 slide through corresponding slots 157 in the housing halves and guide ribs 158 upstanding from the flanges 156 ride against the upper slot walls 160 of the corresponding housing halves for additional transverse stabilization of the axial motion, to reduce patient discomfort.

While particular embodiments of the present invention have been described herein, it will be obvious to those skilled in the art that changes and modifications in various aspects may be made without departing from the broad scope of the invention. Consequently, the scope of the invention is not limited by any particular embodiment but is defined by the appended claims and the equivalents thereof.

The Invention is Claimed as Follows:

1. An actuating mechanism for sequentially advancing and retracting a lancet needle, comprising:
   a) carriage means for advancement and retraction of a lancet needle;
   b) cam-following structure means for transmitting propulsion forces to said carriage means to attain said advancement, without employing an intermediate spring between the cam following structure means and said carrier means;
   c) drive cam structure engagable with said cam-following means for directing said propulsion force thereagainst.

2. An actuating mechanism according to claim 1 wherein said cam-following means comprises a first propulsion surface receiving said directed propulsion force and a second surface engagable with said drive cam structure during said retraction of said carriage means.

3. An actuating mechanism according to claim 2 wherein said first, propulsion surface and said second surface are joined in smooth relative continuation by a third surface formed therebetween.

4. An actuating mechanism according to claim 3 wherein said drive cam structure moves in sequential engagement against (a) said first propulsion surface, (b) said third surface, and (c) said second surface of said cam-following means such that engagement with said third surface corresponds to termination of said carriage means advancement and lancet thrust.

5. An actuating mechanism according to claim 4 wherein said drive cam structure pivots on a pivotal axis thereof during said sequential engagements.

6. An actuating mechanism according to claim 4 wherein said cam-following means is translatable along a reversible linear path corresponding in length to a linear path of said carriage means advancement and retraction.

7. An actuating mechanism according to claim 1 wherein said cam-following means and said drive cam structure are arranged to direct propulsion forces of said carriage means for advancement along a linear path.

8. An actuating mechanism according to claim 7 wherein said drive cam structure pivots in engagement against a first propulsion surface formed on siad cam-following means such that said directed propulsion force is transmitted by siad cam-following means to propel said carriage means along said linear path.

9. An actuating mechanism according to claim 1 further comprising reverse drive means for engaging and propelling said retraction of said carriage means separate from said drive cam structure.

10. An actuating mechanism according to claim 9 wherein said reverse drive means comprises energy transfer and storage means for converting a portion of energy generated by said carriage means advancement and propulsion to potential energy releasable for propelling said carriage means retraction.

11. An actuating mechanism according to claim 10 wherein said energy transfer and storage means comprises spring means energized by said advancement propulsion.

12. An actuating mechanism according to claim 1 wherein said carriage means is integrally formed with said cam-following means.

13. An actuating mechanism according to claim 1 further comprising drive means for generating propulsion of said drive cam structure and said carriage means advancement.

14. An actuating mechanism according to claim 13 wherein said drive means comprises spring means.

15. An actuating mechanism according to claim 14 further comprising cocking means for energizing said spring means.

16. An actuating mechanism according to claim 1 wherein said drive cam structure and a separate reverse drive means are arranged to respectively propel said advancement and retraction of said carriage means in continuous motions thereof in order to thrust and thereafter immediately withdraw said lancet needle.

17. An actuating mechanism for sequentially advancing and retracting a lancet needle, comprising:
   a) carriage means for advancement and retraction of the lancet needle;
   b) cam-following means for transmitting propulsion forces to said carriage means to attain said advancement;
   c) drive cam structure engagable with said cam-following means for directing said propulsion force thereagainst; and
   d) spring means separate from said drive cam structure and energized by said advancement propulsion, releasable for propelling said carriage means retraction; wherein said cam-following means comprises a first, propulsion surface receiving said directed propulsion forces and a second surface engagable with said drive cam structure when said spring means propels said retraction of said carriage means.

18. An actuating mechanism for sequentially advancing and retracting a lancet needle, comprising:
   a) carriage means for advancement and retraction of the lancet needle;
   b) cam-following means for transmitting propulsion forces to said carriage means to attain said advancement;
   c) drive cam structure engagable with said cam-following means for directing said propulsion force thereagainst; and
   d) reverse drive means for engaging and propelling said retraction of said carriage means separate from said drive cam structure, wherein said drive cam structure and said reverse drive means are arranged to propel said advancement and retraction of said carriage means in continuous motions thereof in order to thrust and thereafter immediately withdraw said lancet needle.

19. An actuating mechanism for sequentially advancing and retracting a lancet needle, comprising:
   a) carriage means for advancement and retraction of the lancet needle;
   b) cam-following means for transmitting propulsion forces to said carriage means to attain said advancement;
   c) drive cam structure engagable with said cam-following means for directing said propulsion force thereagainst;
   d) wherein said cam following means comprises a first propulsion surface receiving said directed propulsion force and a second surface engagable with said drive cam structure during said retraction of said carriage means and wherein said first, propulsion surface and said second surface are joined in smooth relative continuation by a third surface formed therebetween and wherein said drive cam structure pivots on a pivotal axis thereof during sequential engagement against (a) said first propulsion surface, (b) said third surface, and (c) said second surface of of said cam-following means such that engagement with said third surface corresponds to termination of said carriage means advancement and lancet thrust, said pivot of said drive cam structure is selectively reversible enabling engagement thereof with said first propulsion surface, third surface, and second surface of said cam-following means in reversible sequence corresponding to said reversible pivot.

20. An actuating mechanism for sequentially advancing and retracting a lancet needle, comprising:
   a) carriage means for advancement and retraction of the lancet needle;
   b) cam-following means for transmitting propulsion forces to said carriage means to attain said advancement;
   c) drive cam structure engagable with said cam-following means for directing said propulsion force thereagainst, wherein said cam-following means comprises a first propulsion surface receiving said directed propulsion and a second surface engagable with said drive cam structure during said detraction of said carriage means, and wherein spring means propels said drive cam structure against said first propulsion surface of said cam-following means, and said drive cam structure engages said second surface of said cam-following means during energizing of said spring means by a cocking means therefor.

21. An actuating mechanism for sequentially advancing and retracting a lancet needle, comprising:
   a) carriage means for advancement and retraction of the lancet needle;

b) cam-following means for transmitting propulsion forces to said carriage means to attain said advancement;

c) drive cam structure engagable with said cam-following means for directing said propulsion force thereagainst, wherein spring means bears against said drive cam structure for generating propulsion of said drive can structure and said carriage means advancement and said drive cam structure reversibly pivots in selective direction forwardly during said propulsion and reversely during energizing of said spring means by a cocking means therefor.

22. An actuating mechanism for sequentially advancing and retracting a lancet needle, comprising:

a) carriage means for advancement and retraction of the lancet needle;

b) cam-following means for transmitting propulsion forces to said carriage means to attain said advancement;

c) drive cam structure engagable with said cam-following means for directing said propulsion force thereagainst, wherein said cam-following means comprises a first propulsion surface receiving said directed propulsion and a second surface engagable with said drive cam structure during said retraction of said carriage means, a spring means propels said drive cam structure against said first propulsion surface of said cam-following means, and said drive cam structure engages said second surface of said cam-following means during energizing of said spring means by a cocking means therefor.

23. An actuating mechanism according to claim 22 wherein said drive cam structure reversibly pivots in direction forwardly during said propulsion and reversely during said energizing of said spring means by said arming means.

* * * * *

UNITED STATES PATENT AND TRADEMARK OFFICE
CERTIFICATE OF CORRECTION

PATENT NO. : 5,318,583
DATED : June 7, 1994
INVENTOR(S) : Richard Rabenau and Rowland W. Kanner It is certified that error appears in the above-indentified patent and that said Letters Patent is hereby corrected as shown below:

Column 7, Line 10 "siad" should read -- said --

Column 9, Line 11 "can" should read -- cam --

Signed and Sealed this

Eleventh Day of October, 1994

Attest:

BRUCE LEHMAN

Attesting Officer

Commissioner of Patents and Trademarks